(12) United States Patent
DeVincenzo

(10) Patent No.: US 6,379,154 B2
(45) Date of Patent: Apr. 30, 2002

(54) SUBPERIOSTEAL BONE ANCHOR

(76) Inventor: John DeVincenzo, 1312 Garden St., San Luis Obispo, CA (US) 93401

( * ) Notice: Subject to any disclaimer, the term of this patent is extended or adjusted under 35 U.S.C. 154(b) by 0 days.

(21) Appl. No.: 09/783,177

(22) Filed: Feb. 14, 2001

Related U.S. Application Data

(63) Continuation-in-part of application No. 09/421,019, filed on Oct. 19, 1999.

(51) Int. Cl.[7] ................................................ A61C 8/00
(52) U.S. Cl. ...................................... 433/173; 433/176
(58) Field of Search ................................ 433/173, 174, 433/175, 176, 201.1; 623/23.49

(56) References Cited

U.S. PATENT DOCUMENTS

| 4,531,916 | A | * | 7/1985 | Scantlebury et al. | ......... 433/173 |
| 5,052,930 | A | * | 10/1991 | Lodde et al. | ................ 433/173 |
| 5,378,152 | A | * | 1/1995 | Elia | ............................ 433/173 |
| 5,427,526 | A | * | 6/1995 | Fernandes | .................... 433/173 |
| 5,571,017 | A | * | 11/1996 | Niznick | ...................... 433/174 |
| 5,853,291 | A | * | 12/1998 | DeVincenzo et al. | ....... 433/176 |

* cited by examiner

Primary Examiner—John J. Wilson
Assistant Examiner—Melba Bumgarner
(74) Attorney, Agent, or Firm—Rodgers & Rodgers

(57) ABSTRACT

A unitary subperiosteal bone anchor having upper and lower portions joined to form a stemplant, and multiple scallops joined to the stemplant and extending outwardly therefrom.

13 Claims, 2 Drawing Sheets

SUBPERIOSTEAL BONE ANCHOR

This is a continuation-in-part of application Ser. No. 09/421,019 filed Oct. 19, 1999.

BACKGROUND OF THE INVENTION

This invention relates to a single leaf stemplant or subperiosteal bone anchor to provide a point of tension for the purpose of moving a dental patient's teeth. A basic problem with known subperiosteal bone anchors is that they require complicated surgical procedures to implant them into a patient's bone. Additionally, known anchors are not readily adaptable to a irregular bone surfaces which impedes osteointegration.

SUMMARY OF THE INVENTION

A subperiosteal bone anchor comprising upper and lower portions joined to form a unitary stemplant and multiple scallops joined to the stemplant and extending outwardly therefrom.

DETAILED DESCRIPTION OF THE INVENTION

Figure 1:
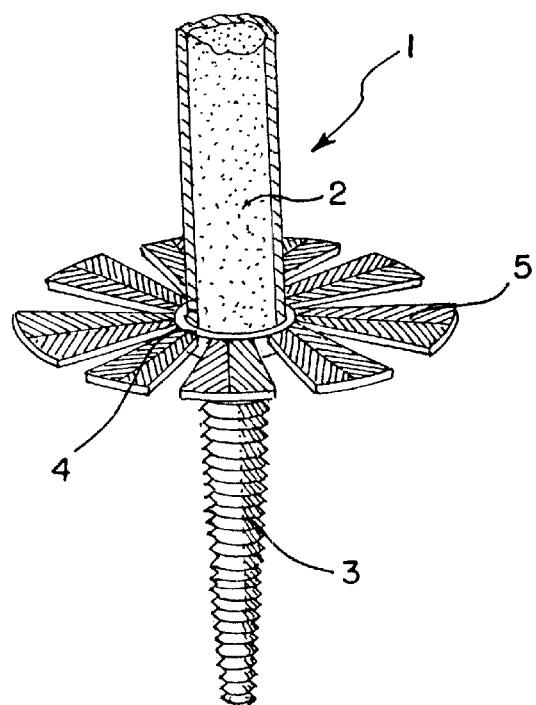
FIG. 1 is a front perspective view of subperiosteal bone anchor according to this invention.

In the drawings, the numeral 1 generally designates the bone anchor constructed according to this invention and which comprises upper portion 2 and lower portion 3 joined together to form an elongated stemplant. Upper portion 2 of bone anchor 1 extends outwardly from a patient's soft tissue and lower portion 3 is installed in a patient's bone. Of course, the shape of upper portion 2 can include a variety of shapes and configurations as necessitated by the particulars of the desired end result. As shown in the drawings, lower portion 3 is threaded so as to allow it to be screwed into the bone. Of course, the threaded grooves can be eliminated and replaced by vertical grooves or staple-like lateral projections. With vertical grooves or lateral projections, the stemplant is simply pounded or driven into position which is a simpler surgical procedure than screwing it into position.

According to one feature of this invention, collar 4 is affixed to the stemplant 1 approximately at the midpoint thereof. To complete the basic elements of the stemplant, multiple scallops 5 are attached to collar 4 by any suitable means such as welding and the like and extend outwardly therefrom. Scallops 5 are thin and are made of any known osteointegratable material. Since scallops 5 are malleable they can be bent upwardly to facilitate insertion of stemplant 1 into the bone and then bent downwardly to conform precisely to the varying contours of the surface of the bone. Lamellar bone strips can be laid over scallops 5 to facilitate osteointegration.

Through clinical research, it has been determined that bone has difficulty in growing over a projection, such as scallops 5, more than 0.015 of an inch thick. In fact, optimumly scallops 5 should be thinner at the peripheries than the remainder of the scallops and the peripheries should be in the range of 0.006 to 0.007 of an inch thick. Also, the relative thinness of scallops 5 allows the practitioner to bend the individual scallops in order to closely approximate the undulations in the adjacent surface of the bone.

To those skilled in the art, it will be understood that since stemplant 1 comprises a single unitary stem comprising upper portion 2 and lower portion 3, scallops 5 are extendable outwardly 360 degrees around stemplant 1 to provide more positioning sites with the maximum number of scallops 5 available for adaptation to the bony surface. Additionally, since scallops 5 closely approximate the surface of the bone, bone overgrowth and resultant osteointegration are enhanced.

Of course, the unitary feature of the stemplant maximizes access to difficult areas in the mouth, facilitates insertion into the bone and eliminates the need for multiple screws or other attachment means. Also, collar 4 provides a definitive stopping point during the insertion procedure. In addition, the single unitary central stemplant is adaptable for increased load capacity by simply increasing the diameter of the stemplant. The length and width of scallops 5 can be increased which allows for added surface contact with the bone.

Figure 2:
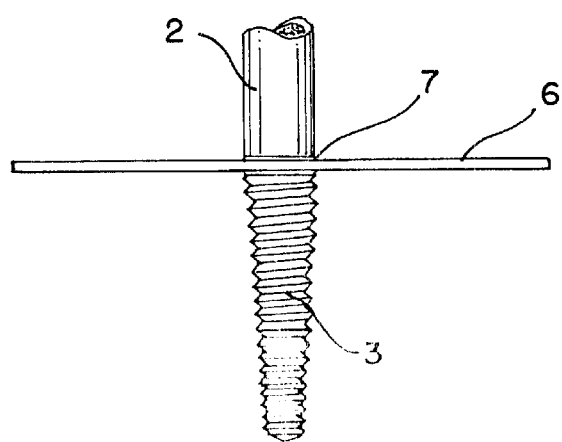
FIG. 2 is a front elevational view of a modified form of the bone anchor shown in FIG. 1.

A variation of the invention is shown in FIG. 2 whereby rigid cap 6 is provided and includes aperture 7. During the insertion procedure, upper portion 2 is inserted through aperture 7 thereby causing cap 6 to overlie scallops 5. Cap 6 is vertically adjustable and is maintained in position by the tension of the overlying periosteum. The purpose of cap 6 is to prevent connective tissue ingrowth and facilitate bone overgrowth.

Figure 3:
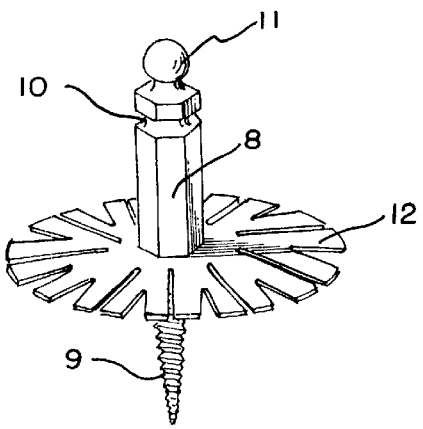
FIG. 3 is a front perspective view of a further modification of the invention.
Figure 4:
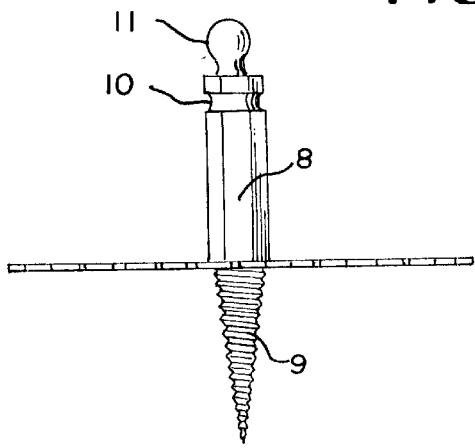
FIG. 4 is a front elevational view of the stemplant shown in FIG. 3.
Figure 5:
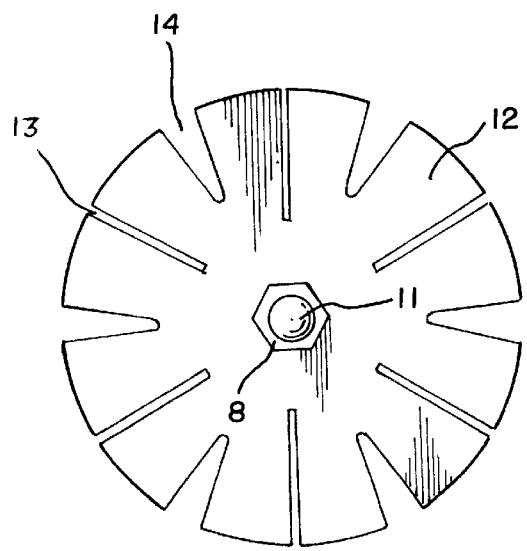
FIG. 5 is a top plan view of the stemplant shown in FIG. 3.

A modification of the stemplant according to this invention is shown in FIGS. 3, 4 and 5 and includes multilateral upper portion 8 and threaded lower portion 9. Indented ring 10 is formed in upper portion 8 and sphere 11 is integrally joined to the top of upper portion 8. Multiple scallops 12 extend from the stemplant generally at the junction between upper portion 8 and lower portion 9. Each scallop 12 is separated from the adjacent scallop by elongated narrow slits 13. Slits 13 provide flexibility in adapting each scallop 12 to the underlying surface of the bone. Further, V-shaped sections 14 are formed in scallops 12 so as to promote migration of bone cells onto the upper surfaces of scallops 12 which substantially facilitates osteointegration.

In FIG. 5, it is readily apparent that the diameter of sphere 11 is less than the distance between parallel sides of multilateral upper portion 8. This is essential whereby a socket wrench can be slipped over sphere 11 and onto multilateral upper portion 8 and manipulated so as to screw threaded lower portion 9 into the patient's bone. Then the desired orthodontic appliance is attached to the stemplant at indented ring 10 so as to effectuate the desired force. Indented ring 10 prevents the vertical migration of the attached orthodontic appliance in the direction of the soft tissue which often occurred in prior stemplants thereby causing them to fail.

Therefore, by this invention, a stemplant is provided which is much quicker to insert because it is simply screwed or pounded into a patient's bone whereas previous devices required attachment by means of separate screws which, of course, requires precise alignment in the drilling process.

Additionally, the use of screws limited the areas in which the stemplant could be placed and required that it be placed where access was the greatest. By this invention, the stemplant can be placed in almost any part of the mouth without having to first tap the one or more screw holes as required for stabilization during the osseointegration process.

What is claimed is:

1. A subperiosteal bone anchor comprising an elongated stemplant, multiple elongated planar scallops attached to said stemplant, said scallops being moldable to conform to the contour of adjacent bone, said stemplant comprising joined lower and upper portions, said scallops extending from the junction of said upper and lower portions 360 degrees around the periphery of said stemplant, said scallops being separated by elongated narrow slits, said scallops extending outwardly equidistantly from said stemplant, and said scallops being equal to or less than 0.015 of an inch thick.

2. A subperiosteal bone anchor according to claim 1 wherein a collar is disposed intermediate said portions.

3. A subperiosteal bone anchor according to claim 2 wherein said scallops extend 360 degrees around the periphery of said collar.

4. A subperiosteal bone anchor according to claim 1 wherein a rigid cap is coaxially disposed with respect to said upper portion and overlies said scallops.

5. A subperiosteal bone anchor according to claim 1 wherein the peripheries of said scallops are thinner than the remainder thereof.

6. A subperiosteal bone anchor according to claim 1 wherein said scallops are of substantially uniform width.

7. A subperiosteal bone anchor according to claim 1 wherein lateral projections are formed on said lower portion.

8. A subperiosteal bone anchor comprising an elongated stemplant, multiple planar scallops attached to said stemplant and extending outwardly therefrom, said scallops being moldable to conform to the contours of adjacent bone, said scallops being separated by elongated narrow slits, and V-shaped cutouts formed in said scallops.

9. A subperiosteal bone anchor according to claim 8 wherein said stemplant comprises an upper portion and a lower portion and wherein said upper portion is of a multilateral configuration.

10. A subperiosteal bone anchor according to claim 9 wherein an indented ring is formed in said upper portion.

11. A subperiosteal bone anchor according to claim 10 wherein a sphere is integrally joined to the top of said upper portion and wherein the diameter of said sphere is less than the smallest cross-sectional dimension of said upper portion.

12. A subperiosteal bone anchor according to claim 9 wherein said lower portion is threaded.

13. A subperiosteal bone anchor comprising an elongated stemplant, multiple elongated planar scallops attached to said stemplant and extending outwardly therefrom, said scallops being moldable to conform to the contours of adjacent bone, said scallops being equal to or less than 0.015 of an inch thick, and a rigid cap coaxially disposed with respect to said upper portion and overlying said scallops.

* * * * *